United States Patent
Hossain et al.

(10) Patent No.: US 8,288,108 B2
(45) Date of Patent: Oct. 16, 2012

(54) EXPRESSION PROFILES FOR PREDICTING SEPTIC CONDITIONS

(75) Inventors: Hamid Hossain, Giessen (DE); Trinad Chakraborty, Giessen (DE); Simon Little, Giessen (DE); Gregor Bein, Wettenberg (DE); Thilo Menges, Linden (DE); Svetlin Tchatalbachev, Giessen (DE)

(73) Assignee: Justus-Liebig-Universitat Giessen, Giessen (DE)

( * ) Notice: Subject to any disclaimer, the term of this patent is extended or adjusted under 35 U.S.C. 154(b) by 623 days.

(21) Appl. No.: 12/104,506

(22) Filed: Apr. 17, 2008

(65) Prior Publication Data

US 2009/0203534 A1 Aug. 13, 2009

Related U.S. Application Data

(63) Continuation of application No. PCT/DE2006/001609, filed on Sep. 14, 2006.

(30) Foreign Application Priority Data

Oct. 21, 2005 (DE) .......................... 10 2005 050 933

(51) Int. Cl.
*C12Q 1/68* (2006.01)
*C12P 19/34* (2006.01)
*C12M 1/34* (2006.01)
*C07H 21/04* (2006.01)

(52) U.S. Cl. .................. 435/6.15; 435/91.3; 435/287.2; 536/23.5

(58) Field of Classification Search .................. None
See application file for complete search history.

(56) References Cited

U.S. PATENT DOCUMENTS

| | | | |
|---|---|---|---|
| 2002/0187476 A1* | 12/2002 | Koroulis et al. | 435/6 |
| 2003/0194752 A1 | 10/2003 | Anderson et al. | 435/7.2 |
| 2004/0157242 A1* | 8/2004 | Ivey et al. | 435/6 |
| 2006/0216707 A1* | 9/2006 | Stuhlmuller et al. | 435/6 |
| 2008/0070235 A1 | 3/2008 | Russwurm et al. | 435/6 |
| 2008/0138832 A1 | 6/2008 | Ivey et al. | 435/7.1 |

OTHER PUBLICATIONS

Prucha et al, "Expression Profiling: Toward an Application Sepsis Diagnostics", Shock, vol. 22, Jul. 2004, pp. 29-33.
Hahn et al, "Burn Injury With Infections Alters Prostaglandin E2 Synthesis and Metabolism", The Journal of Trauma, vol. 47, mo. 6, Dec. 1999, pp. 1052-1057.
Pathan et al, "The Complexity of the Inflammatory Response to Meningococcal Sepsis Revealed by Gene Expressions Profiling using cDNA Microarrays", Critical Care Medicine, vol. 31, No. 12, Feb. 2003, p. A47.
Berner et al, "Elevated Gene Expression of Interleukin-8 in Cord Blood Is a Sensitive Marker for Neonatal Infection", European Journal of Pediatrics, vol. 159, No. 3, Mar. 2000, pp. 205-210.
Takala et al, "Markers of Inflammation in Sepsis", Annals of Medicine, Finnish Medical Society Duodecim, vol. 34, No. 7-8, Oct. 2002, pp. 614-623.
Holmes et al, "Genetic Polymorphisms in Sepsis and in Septic Shock: Role in Prognosis and Potential for Therapy", Chest, The College, vol. 124, No. 3, Sep. 2003, pp. 1103-1115.
Harbarth et al, Diagnostic Value of Procalcitonin, Interleukin-6, and Interleukin-8 in Critically Ill Patients Admitted With Suspected Sepsis, American Journal of Respiratory and Critical Care Medicine, vol. 164, No. 3, Aug. 2001, pp. 396-402.
P.Stafford et al; High-quality microarray data using CodeLink Bioarray Platform; Life Science News 13, 2003 Amersham.

* cited by examiner

*Primary Examiner* — Bradley L Sisson
(74) *Attorney, Agent, or Firm* — Jonathan Myers; Andrew Wilford

(57) ABSTRACT

A rapid, safe method for predicting sepsis, or a condition similar to sepsis, in a mammal is disclosed, which comprises the following steps:
 I) isolating RNA from a biological sample of a mammal;
 ii) labeling the isolated RNA of step I) with a detectable marker;
 iii) hybridizing the labeled isolated RNA of step ii) with at least one DNA of genes Seq.-ID 1 to Seq.-ID 6705 (Table 1), which is spotted onto a microarray and which is a sepsis-specific gene or gene fragment, under the reaction conditions for hybridizations;
 iv) quantitatively recording labeling signals of the hybridized RNA of step iii) in an expression profile;
 v) comparing the expression profile of step iv) with a control sample with respect to a stronger or weaker expression of genes or gene fragments which are specific for sepsis; and
 vi) combining the expression profile of step v) with protein- and metabolite patterns of the biological sample.

2 Claims, No Drawings

EXPRESSION PROFILES FOR PREDICTING SEPTIC CONDITIONS

This application is a continuation of PCT application PCT/DE2006/001609, filed 14 Sep. 2006, published 26 Apr. 2007 as WO 2007/045197, and claiming the priority of German patent application 102005050933.9 itself filed 21 Oct. 2005, whose entire disclosures are herewith incorporated by reference.

The present invention relates to a procedure for the generation and evaluation of expression profiles of a specific group of genes, in order to determine the chance for a sepsis or septic states in the blood sample of a patient.

Introduction into the General Field of Invention

Severe sepsis and septic shock are the leading causes for death in noncardiac intensive care facilities world wide. In Germany, approximately 1% of all inpatients are diagnosed with septic shock every year. The mortality rate for severe sepsis has remained unchanged over the past decades at a level of approximately 40%, in spite of well-known pathogens, target-oriented antibiotic treatments, and adequate supportive immune therapies.

In former beliefs, the pathophysiological concept of sepsis was dominated by immediate toxic effects of microbial compounds on host cells. During the last decade, the focus was changed towards a dysregulated host response itself (tending towards a hyperinflammation) which was considered as organ-damaging: the un-coordinated activation of several pro-inflammatory cascades provokes a reduction in vascular permeability and microcirculation, which again leads to cardio-vascular dysfunctions and organ failure.

The term SIRS ("Systemic Inflammatory Response Syndrome") describes this dysregulated systemic inflammatory cascade, which impairs macro- and microcirculation profoundly and consecutively leads to multiorgan damage. The most important initial event for SIRS are severe infections with bacteria and/or bacterial structural components such as endotoxins and various exotoxins invading the intravasal- and/or lymphatic space. The interaction with key molecules of the immune defense triggers a generalized inflammatory reaction with systemic release of biological mediators such as cytokines (primarily interleukin-1 and TNFa), activated complement components, coagulating factors, and lipid mediators. Basically every infection can degenerate into a sepsis.

Other triggers of SIRS are severe polytraumas, burns and extensive tissue necroses. However, it is still unclear to date if these initially non-infectious elicitors in fact represent a "sterile" SIRS, or if also a secondary invasion of pathogens and/or the entry of bacterial toxins into the systemic circulation after a loss of barrier function and host defense potential is mainly involved, since only a few hours after a trauma, an extensive burn or a proceeding pancreatitis, an impairment of granulocyte function can be observed. Changes in chemotaxis, adherence, phagocytotic capacity and the so-called "oxidative burst" are indicative for this process of an impaired cellular immune function.

It is well known from clinical observations and experimental infection models that the individual resistance or susceptibility to pathogens is, among others, determined by genetic factors. In the human genome, a base exchange (single nucleotide polymorphism, SNP) can be found once every 1000 base pairs, which occurs with a frequency of 1% in a given population. This results in approximately three million variants, considering the size of the human genome. Some of these variants are functionally or pathologically relevant, since they are located in those regions of a gene which influence gene expression or result in an amino acid exchange. These variants may, for example, lead to a resistant or susceptible phenotype in the individual immune response to a pathogen. In general, several different genes act together in a complex manner to determine a specific phenotype with respect to the immune response.

Some clinically relevant variants of genes involved in the immune response to pathogens have already been identified in the past. An interesting example are polymorphisms of immune response genes, which have been associated with different courses of the disease after bacterial infections. For example, variants of the plasminogen activator inhibitor type 1 (PAI-1) were associated with the risk of a shock in the context of a meningococcal disease and with lethality after polytraumas. A SNP in the promoter region of the tumor necrosis factor alpha gene was associated with the mortality rate in the context of septic shock.

For an assessment of polymorphisms, the prognostic importance is determined by several single parameters which can to date only be investigated to some extent and on no account completely by examination of one single gene polymorphism.

The diagnosis of sepsis is based on the occurrence of different inflammatory reactions, also known as systemic inflammatory response syndrome (SIRS), which affect the entire organism. Characteristically, at least two typical symptoms appear such as:

A body temperature above 38° C. or less than 36° C.
Pulse frequency above 90 beats per minute
Respiratory rate above 20 breaths per minute
Increased number of white blood cells (leukocytes >12.000/mm$^3$ or <4.000/mm$^3$, or 10% immature)

These symptoms are however not very specific, since they also occur in a variety of patients with other diseases.

A severe sepsis is characterized by a reduced organ blood circulation, decreased blood pressure and organ dysfunction. A dysfunction of several organs due to sepsis is called "multiple organ dysfunction syndrome" (MODS).

An urgent demand exists for an early, differentiated and reliable diagnosis of sepsis. An ideal indicator of sepsis should allow an early diagnosis and help to differentiate infectious from noninfectious forms of systemic inflammations. Furthermore, it should be possible to obtain information concerning the course of the disease, severity, and possible outcome. At present, none of the known potential markers for sepsis (i.e. C-reactive protein, procalcitonin) meets the expectations of physicians completely.

A differentiated and reliable diagnosis of sepsis is a prerequisite for the administration of the correct therapy. The earlier this is possible, the higher are survival rates, because the risk of organ dysfunctions is being reduced.

Patients with sepsis, particularly those with a septic shock, require cost intensive in-patient intensive care treatment. This includes among other things the application of antibiotics, blood pressure increasing drugs and machine support for organ dysfunctions.

The prior art knows only the microbial analysis of patient samples for the identification of the infectious agent. These procedures are time-consuming, and unfortunately, the infectious agent can only be identified in 15-20% of all septic patients. Approximately 25-40% of the patients die despite an antibiotic therapy and intensive care treatment, and often, because the sepsis has been discovered too late.

The development of the microarray technology allows the simultaneous analysis and comparison of 10.000 genes and their expression products. Gene expression profiles generated in this way are used e.g. for cancer diagnostics.

In DE 10315031 it is proposed to use gene expression profiles for the diagnosis of sepsis. However, the assessment of gene expression alone is only one building block of the system which is responsible for the development of disease states, and thus allows only limited insight into the relevant mechanisms of pathogenicity.

Only a system biology approach including all available system data like e.g. from the genome (genome typing), transcriptome (gene expression), proteome (protein-/metabolite determination) and phenotype (laboratory-/vital parameters) allows a comprehensive insight into the processes which contribute to disease development, thus leading to an improved diagnostics.

Object

It is the object of the present invention to provide a reliable and differentiated procedure for the diagnosis of sepsis and/or septic states in the blood of patients, which takes into account clinical and genomic data generated from the blood of these patients.

Solution

This object is solved by invention of a procedure according to claim 1 and the expression profile obtained with this procedure, which is correlated with clinical and genomic data.

The procedure according to the present invention for the diagnosis of sepsis and/or septic states in the blood of patients with infections allows a considerably earlier detection of the disease than possible using clinical criteria. Already approximately 4-7 days prior to the clinical manifestation of a septic state, indications for an anticipated septic reaction can be obtained, and thus appropriate precautions can be taken.

The procedure according to the present invention includes the thorough preparation of the biological sample, in particular the preparation of blood deriving from a mammal, particularly from a human, and allows an RNA extraction from the whole blood, which allows a fast and permanent stabilization of the RNA as well as the extraction of sufficient amounts of RNA from as little whole blood as possible in the clinical everyday routine.

Expression profiles are established using genes which were, after analysis of clinical, laboratory and genomic data, recognized as highly relevant for the prediction of sepsis.

EMBODIMENTS

For the establishment of optimal gene expression profiles, a prospective patient study is conducted to investigate the host response to a severe infection or a severe trauma. Herein, critically ill patients are recruited and their clinical, laboratory chemical and genomic data are collected and combined to allow conclusions about development and course of a sepsis. Questions to be asked are:
1) Is it possible to stratify patient groups on the basis of expression profiles?
2) Does gene expression of patients with or without sepsis differ?
3) Is it possible to distinguish early and late phases of sepsis based on expression patterns?
4) Is it possible to identify organ-specific patterns of gene expression?
5) Does the expression pattern allow predictions concerning a sepsis?
6) Is it possible to use the expression pattern prognostically?
7) Is it possible to identify biomarkers which can be used as surrogate marker for the course or outcome of the disease?

Initially, three patient cohorts are investigated (adult patients with polytraumas, adults with severe pneumonia, preterm infants born earlier than week 32 of pregnancy) and thereby, clinical and genomic data generated from the blood of these patients are evaluated to draw conclusions concerning the course of disease and prognosis of sepsis. Important criteria are regulations for the enrollment of patients (inclusion/exclusion criteria), regulations for blood withdrawal (time points, blood sampling system), regulations for transport and storage of samples, and regulations for the input of clinical and person-related data.

The biological sample (e.g. blood) is processed with a specific technique in order to obtain reliable and differentiated results which are also suitable for routine diagnostics.

The procedure according to the present invention for the in-vitro detection of sepsis and/or sepsis-related states in a biological sample from a mammal incorporates the following steps:
i) Isolation of RNA from the biological sample of a mammal
ii) Labeling of RNA of step i) with a detectable marker
iii) Hybridizing of RNA of step ii) with DNA which is arranged in a microarray and which is at least one gene or gene fragment specific for sepsis, using the reaction conditions for hybridization
iv) Quantitative recording of signals from the hybridized RNA of step iii) in an expression profile
v) Comparison of the expression profiles of step iv) with a control sample in regard to a stronger or weaker expression of genes or gene fragments which are specific for sepsis
vi) Combination of the expression profile of step v) with protein and metabolite patterns of the biological sample 1. Sample Preparation As a sample, biological material of a mammal such as liquor, urine, tracheal secrete, seminal liquid, ascites fluid, sputum, puncture fluid or lymph fluid, preferably blood, is used.

Blood withdrawal is preferably performed using commercially available PaxGene tubes according to the manufacturer's instructions (PreAnalytix GmbH, Switzerland). Blood from preterm infants is available as umbilical cord blood.

Two times 750-800 µl PaxGene-solution and two times 250-300 µl umbilical cord blood are each given into a separate sterile cuvette, e.g. a plastic or glass cuvette. Blood from adults is available as whole blood. Two times 2.5 ml whole blood is given into a tube which is filled with PaxGene-solution and ready for use. Samples are stored in PaxGene tubes for 2-4 hours at room temperature, followed by freezing at −80° C. Under these conditions, samples can be stored for years. The advantage of the blend of reagents of the PaxGene tubes is a quick and permanent stabilization of the RNA. This ensures that even if transportation is delayed (clinical everyday life), the RNA is not degraded.

Alternatively, EDTA-blood can be taken, but in this case transportation and RNA-extraction has to be carried out immediately. RNA extraction is then performed using general procedures.

2. RNA Processing

Initially, RNA-isolation from samples of step 1 is performed according to standard techniques, e.g. according to the PAXgeneä Blood RNA Kit (PreAnalytix) instruction manual. Isolated RNA is then purified using a specific protocol for precipitation in order to improve RNA quality:

A. Addition of 0.1 volumes 3 M sodium-acetate, pH 5.2, and 3 volumes ethanol (98%) to the RNA-extract.
B. Mix and incubate mixture at −20° C. for 4 hours or at −80° C. for at least 1 hour to precipitate RNA.
C. Centrifugation of the mixture at 12 000×g for 30 minutes at 4° C.
D. Wash RNA pellet with 2 volumes 75% (v/v) ethanol for 2 min.
E. Centrifugation of the mixture at 12 000×g for 5 min at 4° C. Alternatively, repeat step D.
F. Dry pellets in a SpeedVac without heating and dissolve RNA in 35 µl sterile $H_2O$.

Finally, RNA is quantified e.g. by Nanodrop measurement, and RNA quality can be determined using the Agilent Bioanalyzero.

3. In-vitro-transcription and Hybridization

Prior to further treatments, RNA samples exhibit a regular Agilent profile and a wavelength ratio 260/280 of 1.8-2.1. Labeling and transcription of RNA into fluorescence-labeled cRNA is performed with 2 µg RNA, using e.g. the "CodeLink Expression Assay Reagent Kit, Manual Prep" (Amersham Biosciences) according to the "CodeLink Target Labelling and Array Hybridisation" protocol. For fluorescence labeling, streptavidin-Cy5 is used, but labeling can also be carried out with other common fluorescence markers. The labeled cRNA is then tested with respect to RNA quality and quantity. 30 µg cRNA are fragmented and hybridized in triplicates to CodeLink Human Set I Microarrays (Amersham Bioscience) on a shaker over night at 37° C. Staining and washing of the arrays is performed in appropriate devices according to the manufacturer's protocol (Amersham Biosciences). Finally, arrays are scanned using Genepix 4000b Axxon Instr. (Molecular Dynamics).

Alternatively, dyes or radioactivity markers can be used, which is well known to those skilled in the art and can be carried out with commercially available materials.

It is generally known that it is difficult to use blood, particularly blood from infants, as source of the transcriptome for diagnostic purposes. The procedure according to the present invention overcomes this problem and demonstrates that samples which are prepared in this way are ideally suited for their use in expression analyses and represent a reliable, easy-to-obtain diagnostic instrument.

Altogether, microarrays of different sources and compositions allow the simultaneous analysis of 10 000 to 50 000 genes. For example, with the CodeLink Human Set I Microarrays (Fa. Amersham Bioscience), 9 945 genes can be investigated. Among these, approximately 6 710 genes are differentially regulated in patients with or without sepsis over a period of 14 days, whereby the criterion which defines differential regulation is 0.5<standard deviation of the expression intensity <10. The 6 710 genes are listed in table 1.

Using statistical procedures such as e.g. Rankproducts (RP), Statistical Analysis of Microarrays (SAM), EDGE, or a different suitable method, statistically significantly regulated genes can be estimated with a type-1 error (e.g. false discovery rate (=FDR) or p-value as a measure for the estimation of false-positive genes) that is chosen by the user.

By changing the FDR- or p-value, the number of significant genes also changes. In principle, the range of FDR can vary from being very low, like e.g. 0.02% with only 20 significant genes or 1% with 120 genes, to high like e.g. 50% with approximately 1 000 genes. The higher the FDR, the higher is the number of regulated genes, but also the number of possible false-positive genes. It is important to chose an FDR which is high enough to include as many genes as possible, which might be involved in the process, but at the same time keeps the number of false-positive genes in an acceptable range, like e.g. an FDR of 30% which includes all genes from 0% to 30% and thus also the highly significant genes, while the number of false-positive genes is still in a generally acceptable range.

The time span between trauma and admission to the hospital (shock room, intensive care unit) varies from patient to patient. Investigations showed that a distinction between patients with or without sepsis using gene expression profiles is already possible when a patient is admitted. These profiles are preferably established within 6 to 24 hours after trauma, since during this time span the distinction between septic/non-septic becomes apparent (corresponding roughly to the point of admission to the intensive care unit). Alternatively, expression profiles are established earlier, e.g. on admission to the shock room.

The number of significantly regulated genes, for instance at the time of admission to the intensive care unit, is in the range of approximately 860 genes (FDR=30%) between patients with and without sepsis, reflecting the statistically/biologically relevant gene expression at this early time point. Table 2 lists these 860 genes.

Already one day later, the number of significantly regulated genes increases to approximately 1 400 genes (table 3) and remains constant at about 1 100 genes on day 3 (table 4). Between day 4 and day 7, the number of significantly regulated genes drops down to approximately 270 genes max. (table 5). This corresponds to the period when the septic state reaches its maximum and a sepsis can be diagnosed clinically. On day 9, the number of significantly regulated genes reaches again approximately 1 100 genes (table 6). With RP, the number of significantly regulated genes during this course of time added up to 2 530 genes with an FDR=30% (table 7) altogether.

This profile of numbers of significantly regulated genes in the course of time with initially increasing number of genes until day 3 after admission to the intensive care unit, followed by a drastic decrease between day 4 and 7 and again increase in numbers from day 8 on to the level of day 3, reflects very well the clinical course of the patient. In most cases, a sepsis is diagnosed between day 4 and 7 and is then often associated with an immune paralysis. By using expression profiles, genes and thus also the mechanisms which contribute to this phenotype can be identified.

Genes detected in the course of time, but most of all genes detected at the time point of admission to the intensive care unit, are candidates for the determination of a predisposition to sepsis and are used diagnostically according to the present invention in order to identify patients who have an increased risk to die of sepsis. Moreover, at this time point genes can already be identified whose detectable gene products (proteins) are associated with specific clinical symptoms during the further course of disease. Thus it is also possible to predict early symptoms of a sepsis as well as to prognose the severity of disease which is to be expected.

On admission, the expression patterns of patients show distinct differences between patients who will or will not develop a sepsis a few days later. Based on these patterns, patients who may develop a sepsis during their stay as inpatient can be identified at an early stage. These groups of genes (table 7) are closely monitored via expression profiles and serve as diagnostic markers to predict the onset of a sepsis. The early identification of these patients results in increased control measures and a different therapeutic regimen.

Furthermore, expression profiles which are established during an in-patient stay can be used for follow-up examinations of patients with polytraumas/severe infections (table 2 to 6).

Expression patterns which are established during the in-patient stay show that in patients developing sepsis, the transcriptional/cellular activity of a large group of genes is turned off more and more. This becomes evident by a down-regulation of genes belonging to various functional groups (e.g. innate and acquired immunity, apoptosis, transcription factors, and metabolism). This deactivation of cellular activity/transcription cannot be observed in patients who will not develop a sepsis. Simultaneously with the reduced transcription of the afore mentioned gene groups, the expression of genes of other functional groups is enhanced, most of all genes of the innate immune response. This activation of evolutionary ancient genes like e.g. defensins can be interpreted as a mobilization of residual host defense functions of every single cell.

This profile of an early down-regulation of transcriptional/cellular activity can diagnostically be interpreted as an aggravation of condition and as sign of a beginning sepsis.

Independently of the level of transcriptome (level 1), laboratory parameters which are part of the standard diagnostics in intensive care units like hemogram, CRP, PCT, liver- and kidney parameters, electrolytes etc. are determined routinely. These laboratory parameters represent to some extent the level of the proteome (level 2). In addition, proteins (gene products) which are not routinely assessed can also be determined on the basis of their gene expression. Not only proteins, but also metabolites which are produced as intermediates in metabolic pathways (like e.g. TNF-α, glycolysis or gluconeogenesis, fatty acid cycle) are determined. Thus, gene expression profiles are combined with protein and metabolite patterns. This combination of transcriptome and proteome enhances the significance, since here biologically active intermediates and end products of gene expression, i.e. gene products (proteins) or metabolites, are also recorded and thus contribute to the profile.

Furthermore, vital parameters such as blood pressure, heart rate, body temperature etc. are determined. These parameters are part of the standard diagnostics in intensive care units and represent the level of phenotype (level 3). Thus, transcriptome, proteome, and phenotype are combined in any possible way, further enhancing the biological relevance of the findings.

The level of the genome (level 0) is investigated by mutation screening of patients (analysis of polymorphisms, SNP=Single Nucleotide Polymorphism). SNP-analyses are performed both depending on the gene expression analysis via identification of hot spots on the chromosome and independently of gene expression using already published data. By investigating the genome, the path from genotype to phenotype is described completely, and a combination of the four levels allows the association of a disease state (phenotype) with a genotype, leading again to an increased biological relevance of the findings.

In genotyping studies of well-known SNPs of the TNF-gene (TNF-1032A>G (rs1799964), TNF-863C>A (rs1800630), TNF-857C>T (rs1799724), TNF-308G>A (rs1800629), TNF-238G>A (rs361525), TNF 488C>T (rs1800610), TNF 859A>G (rs3093662)) as well as LTA-252A>G (rs909253) and LTA-80C>A (rs2239704) in 159 Caucasian patients with severe traumas, an association between certain SNPs and an increased incidence and mortality of sepsis could be detected:

For example, TNF-308A and LTA-252G alleles are significantly ($P<0.0001$) associated with increased levels of TNF-α in the blood (here: blood plasma) of patients with severe traumas on the day of admission and consecutive 14 days.

The TNF-308A, LTA-252G and LTA-80A alleles are furthermore significantly ($P<0.0001$; $P<0.042$; $P<0.031$) associated with the incidence of sepsis in patients with severe traumas.

Furthermore, TNF-308A (rs1800629) and LTA-252G (rs909253) alleles are significantly ($P<0.0001$; $P<0.0002$) associated with lethal outcome in patients with severe traumas.

The genotyping of patients with respect to TNF-308A (rs1800629), LTA-252G (rs909253), and LTA-80A (rs2239704), and the continuous measurement of TNF-α-levels in the blood (here: blood plasma) of e.g. traumatized or otherwise severely ill patients from the beginning on are thus highly valuable for an early identification of patients who might develop a sepsis and, on the other hand, for the prognosis of the disease (here: death).

For patients with these genotypes, expression profiles can be established on admission or later on, which differ from profiles of patients without these genotypes. These profiles can be utilized diagnostically e.g. as "death signatures" (table 8) to identify risk patients on the one hand and the monitor the progredience of the disease at an early state on the other hand. Based on genotype and expression profile, relevant proteins and levels thereof in body fluids such as e.g. blood, urine, liquor, tracheal secrete, seminal liquid, ascites fluid, sputum, puncture fluid, or lymph fluid can be determined, which again contributes to the phenotype. Therapeutical strategies aimed at metabolic pathways of these proteins can influence the outcome and thus alter the phenotype.

The invention uses expression profiles (level 1) and a combination thereof with other levels (protein levels, vital parameters, genotype) in order to a) stratify patients independently of the disease state (thus, patients can be reclassified in other categories which were not thought of before)
b) classify patients (e.g. risk patient/no risk patient)
c) diagnose early a septic disease state (e.g. already on admission of the patient)
d) identify early and monitor the course of the disease (=progredience/improvement, e.g. liver- or kidney failure)
e) prognose the outcome of the disease (e.g. death/survival), allowing an improved assessment of the disease state and thus a well adapted therapy. Monitoring the course of differentially regulated genes (table 1), not only conclusions can be drawn concerning commonly regulated genes, but also insight is gained into the individual gene regulation of every single patient. Thus, the therapy can be adjusted individually at any time.

Furthermore, based on the genes in these expression profiles conclusions can be drawn concerning the cell types which contributed to this profile (e.g. monocytes, granulocytes). This allows an identification of those cell types which participated in the development of septic states and the progredience.

In this case, the quantitative determination of these cell types itself may serve as a marker for the course of the disease.

Similarly, genotypes, expression profiles, protein patters, laboratory and vital parameters (=components of all four levels) represent biomarkers which individually or in combination can be used as surrogate markers for the course of a disease or disease outcome (e.g. death/survival). These surrogate markers could e.g. be used in manifold ways in clinical and pharmacological studies to e.g. predict the outcomes early and thus reduce duration and costs of a study.

Another embodiment of the present invention is a sepsis-array for adults and prematurely born infants. For this purpose, a microarray is established which is based on the genes which are differentially regulated in the course of a developing sepsis and which are involved in the development of an inflammatory response and sepsis in adults and preterm infants.

This chip for a diagnosis of sepsis is already widely used in diagnostics and is also applied for large patient collectives. According to a sepsis array with genes (oligonucleotides), a sepsis-specific protein chip is produced.

This sepsis-specific protein chip comprises gene products (e.g. proteins) of genes which are differentially regulated in the course of a developing sepsis, genes listed in table 1 (Seq.-ID 1 to Seq.-ID 6705), preferably genes chosen from table 7 and 8). Using sepsis-specific protein chips, body fluids such as e.g. blood (plasma, serum), urine, liquor or tracheal secrete can immediately be screened for the presence of these gene products.

For the fabrication of microarrays, genes Seq.-ID 1 to Seq.-ID 6705 are used.

The present invention offers the possibility to characterize a disease process and describe and/or predict early the outcome using transcripts and their patterns. It is a method which can be referred to as transcriptology.

The evaluation of expression analyses is performed in close relation to other patient-related data using a database structure in which all relevant data are structurally and semantically standardized and collected in a sufficiently pseudonymized form according to data protection standards. This is implemented in databases which were specially generated for these studies, GRID (GRID-DB) and PIRO (PIRO-DB). The inclusion of a patient into the evaluation of expression analyses and thus defining his data as being relevant is carried out by entering the ID in the GRID-DB, which contains all patient-related personal data, inclusion and exclusion criteria, and all diagnoses. Disease-relevant scores are calculated using the GRID-DB. All data are exported as text files into the Piro database (PIRO-DB).

Data recorded with PDMS (Patient Data Management System) are stored in an Oracle™-database, which is similar in structure to the HL7-model (ICU Data). From the raw data which are only accessible for system administrators, data relevant for the study are extracted by SQL-commands which are implemented in the database, pseudonymized and presented as database view to the domain specialists (DS). In this pseudonymized section, auxiliary tables are generated for the standardization, chronological arrangement, and aggregation of data.

From ICU Data, auxiliary tables are generated by a save-data function which is integrated in Oracle™ and corresponds to the Entity-Attribute-Value (EAV) data model. From these auxiliary tables, text files are generated using SQL-scripts which are transferred into a relational Oracle database (PIRO-DB) where they represent the clinical data mart for clinical and biological research. From this data, a PIRO-score (Predisposition, Infection, Response, Organ dysfunction) is generated for the early diagnosis and prognosis of sepsis patients.

Using a combination of these database systems, it is possible to integrate patient data from the clinical routine documentation and data from clinical and biological research, which forms the basis for the identification of specific disease-associated gene expression patterns and the development of combinatory scoring-systems for a precise and early diagnosis and the prediction of disease outcome.

Additionally, new software programs are developed and integrated into the evaluation of gene expression profiles.

The QuBE (Query Building Environment) is a user-friendly Perl- and Java-script, allowing individual as well as complex queries of the PIRO-DB with respect to patient-related, clinical, laboratory-chemical, and genomic data. (Source code 1).

The DataManager is a data integration software, written in Pascal (Boland-Delphi 6), which at first sorts large data volumes generated from microarrays automatically according to patients into respective files (source code 2). Furthermore, the program identifies missing data in the arrays which are replaced by mean values from technical replicates of respective microarrays. In addition, the program calculates various parameters which are indicative for the quality of an array (e.g. number of expressed genes, number of spots with average intensities lower than the average local background). Advantages of the DataManager are improved data integration and data processing as well as decision making which arrays should be used in the analyses. This is particularly important with regard to the use of arrays as diagnostic means. A corruption of data due to substandard arrays is avoided. QuBe combines data from microarrays with clinical data and shows the correlation between transcriptome and phenotype. This information aids the assignment of expression profiles to a clinical phenotype.

Furthermore, commercially available software programs such as Imagene, CodeLink Batch Submission and Expression Analysis, Avadis, Dchip, SAM, Genesis are used.

Table 1 shows differentially regulated genes of polytrauma-patients with and without sepsis in the course of 9 days without indication of relative changes; Seq.-ID 1-6706

ACC=Accession number; symbol=gene symbol; LLID=LocusLink-ID and gene-ID, respectively. No indication of relative changes, since these genes are regulated together as well as individually in patients with and without sepsis. Criterion for differential regulation: 0.5<standard deviation of expression intensity of each gene for each patient <10

Table 2 shows significantly over- and underexpressed genes of polytraumatized patients with sepsis as compared to a control group of polytraumatized patients without sepsis at the time point of admission; Seq.-ID 6706-7563

ACC=accession number; Symbol=gene symbol; LLID=LocusLink-ID and gene-ID, respectively; Pat. 1 to 10=relative changes in gene expression of respective patients with sepsis as compared to the control group on admission; FC=Fold Change and relative change in gene expression of the patient group with sepsis as compared to the control group on admission, respectively Table 3 shows significantly over- and underexpressed genes of polytraumatized patients with sepsis as compared to a control group of polytraumatized patients without sepsis, 24 hours after admission; Seq.-ID 7563-8948

ACC=accession number; Symbol=gene symbol; LLID=LocusLink-ID and gene-ID, respectively; Pat. 1 to 10=relative changes in gene expression of respective patients with sepsis as compared to the control group 24 hours after admission; FC=Fold Change and relative change in gene expression of the patient group with sepsis as compared to the control group 24 hours after admission, respectively Table 4 shows significantly over- and underexpressed genes of polytraumatized patients with sepsis as compared to a control group of polytraumatized patients without sepsis, 3 days after admission; Seq.-ID 8948-10041

ACC=accession number; Symbol=gene symbol; LLID=LocusLink-ID and gene-ID, respectively; Pat. 1 to 7=relative changes in gene expression of respective patients with sepsis as compared to the control group 3 days after admission; FC=Fold Change and relative change in gene expression of the patient group with sepsis as compared to the control group 3 days after admission, respectively Table 5 shows significantly over- and underexpressed genes of polytraumatized patients with sepsis as compared to a control group of polytraumatized patients without sepsis, 5 days after admission; Seq.-ID 10041-10306

ACC=accession number; Symbol=gene symbol; LLID=LocusLink-ID and gene-ID, respectively; Pat. 1 to 7=relative changes in gene expression of respective patients with sepsis as compared to the control group 5 days after admission; FC=Fold Change and relative change in gene expression of the patient group with sepsis as compared to the control group 5 days after admission, respectively Table 6 shows significantly over- and underexpressed genes of polytraumatized patients with sepsis as compared to a control group of polytraumatized patients without sepsis, 9 days after admission; Seq.-ID 10306-11379

ACC=accession number; Symbol=gene symbol; LLID=LocusLink-ID and gene-ID, respectively; Pat. 1 to 10=relative changes in gene expression of respective patients with sepsis as compared to the control group 9 days after admission; FC=Fold Change and relative change in gene expression of the patient group with sepsis as compared to the control group 9 days after admission, respectively Table 7 shows significantly over- and underexpressed genes of polytraumatized patients with sepsis as compared to a control group of polytraumatized patients without sepsis in the course of 9 days; Seq.-ID 11379-13905

ACC=accession number; Symbol=gene symbol; LLID=LocusLink-ID and gene-ID, respectively; FC__1 to 9=Fold Change and relative change in gene expression of the patient group with sepsis as compared to the control group, respectively, on admission (FC__0), after id (FC__1), 3d (FC__3), 5d (FC__5), and 9d (FC__9)

Table 8 shows significantly regulated genes of polytraumatized patients with sepsis and lethal outcome as compared to polytraumatized patients with sepsis but without lethal outcome at the time of admission ("Death Signature"); Seq.-ID 13906-14075

ACC=accession number; Symbol=gene symbol; LLID=LocusLink-ID and Gene-ID, respectively; FC=Fold Change and relative change in gene expression of the patient group with sepsis and lethal outcome as compared to patients with sepsis but without lethal outcome at the time of admission Lengthy table referenced here

US08288108-20121016-T00001

Please refer to the end of the specification for access instructions.

Lengthy table referenced here

US08288108-20121016-T00002

Please refer to the end of the specification for access instructions.

Lengthy table referenced here

US08288108-20121016-T00003

Please refer to the end of the specification for access instructions.

Lengthy table referenced here

US08288108-20121016-T00004

Please refer to the end of the specification for access instructions.

Lengthy table referenced here

US08288108-20121016-T00005

Please refer to the end of the specification for access instructions.

Lengthy table referenced here

US08288108-20121016-T00006

Please refer to the end of the specification for access instructions.

Lengthy table referenced here

US08288108-20121016-T00007

Please refer to the end of the specification for access instructions.

Lengthy table referenced here

US08288108-20121016-T00008

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US08288108B2). An electronic copy of the table will also be available from the USPTO upon request and payment of the fee set forth in 37 CFR 1.19(b)(3).

The invention claimed is:

1. A method for in-vitro detection of sepsis in a blood sample of a human inpatient selected from the group consisting of a polytraumatized adult patient, an adult patient with pneumonia, and a prematurely born infant, the method comprising the following steps:
   i) extracting RNA from a blood sample of the human inpatient;
   ii) quantifying the RNA extracted during step (i), and transcribing and labeling the RNA extracted during step (i) to obtain a quantity of labeled cRNA, wherein for labeling a detectable marker is used, wherein said detectable marker is a fluorescence marker, dye marker or a radioactive marker;
   iii) fragmenting the labeled cRNA obtained according to step (ii), and specifically hybridizing the labeled, fragmented cRNA, if present with polynucleotides on a microarray comprising DNA which corresponds to polynucleotides SEQ ID NO: 2 and SEQ ID NO: 6704 (Table 1) to obtain labeled, fragmented, hybridized cRNA;
   iv) obtaining control labeled and fragmented cRNA from a human with no sepsis wherein said control labeled fragmented cRNA is obtained in accordance with steps (i), (ii) and (iii), and hybridizing a known quantity of the control labeled, fragmented cRNA to said microarray in accordance with step (iii);
   v) determining a quantitative expression profile for both the human inpatient and the control labeled cRNA; and
   vi) comparing the expression profiles of step (v) of the human inpatient and of the control wherein statistically significant overexpression of the gene corresponding to SEQ ID NO: 2 and statistically significant underexpression of the gene corresponding to SEQ ID NO: 6704 for the human inpatient relative to the control is indicative of the patient's having sepsis.

2. A DNA-microarray for diagnosis of sepsis in a blood sample of a human, said microarray consisting of at least one of the following groups:
   SEQ ID NO: 6706 to SEQ ID NO: 7562 (Table 2),
   SEQ ID NO: 7563 to SEQ ID NO: 8947 (Table 3)
   SEQ ID NO: 11379 to SEQ ID NO: 13905 (Table 7), and
   SEQ ID NO: 13906 to SEQ ID NO: 14075 (Table 8),
   wherein said oligonucleotides are the only oligonucleotides forming the microarray.

* * * * *